United States Patent [19]

Müller et al.

[11] Patent Number: 5,066,401

[45] Date of Patent: Nov. 19, 1991

[54] FLAT OR CAPILLARY MEMBRANE BASED ON A HOMOGENEOUS MIXTURE OF POLYVINYLIDENE FLUORIDE AND A SECOND POLYMER WHICH CAN BE RENDERED HYDROPHILIC BY CHEMICAL REACTION

[75] Inventors: Heinz-Joachim Müller, Wörth am Main; Heinz-Dieter Sluma, Grossostheim; Günter Eberhard, Erlenbach; Ernst Spindler, Obernburg; Lothar Krauss, Erlenbach; Helmut Völker, Klingenberg, all of Fed. Rep. of Germany

[73] Assignee: AKZO N.V., Netherlands

[21] Appl. No.: 552,051

[22] Filed: Jul. 13, 1990

[30] Foreign Application Priority Data

Jul. 13, 1989 [DE] Fed. Rep. of Germany ....... 3923128

[51] Int. Cl.$^5$ .............................................. B01D 71/34
[52] U.S. Cl. ............................ 210/500.35; 210/500.42
[58] Field of Search ...................... 264/41, 45.1; 55/16, 55/158; 210/500.42, 500.35; 521/53, 918, 145

[56] References Cited

U.S. PATENT DOCUMENTS

| 4,776,959 | 10/1988 | Kasai et al. | 210/500.42 |
|---|---|---|---|
| 4,943,373 | 7/1990 | Onishi et al. | 210/500.42 |

FOREIGN PATENT DOCUMENTS

| 0040670 | 12/1981 | European Pat. Off. . |
|---|---|---|
| 0186758 | 7/1986 | European Pat. Off. . |
| 0250337 | 12/1987 | European Pat. Off. . |
| 2735443 | 2/1978 | Fed. Rep. of Germany . |
| 2822266 | 12/1978 | Fed. Rep. of Germany . |
| 3218502 | 11/1982 | Fed. Rep. of Germany . |
| 3129744 | 3/1983 | Fed. Rep. of Germany . |
| 3329578 | 3/1985 | Fed. Rep. of Germany . |
| 3509068 | 9/1986 | Fed. Rep. of Germany . |
| 3631561 | 3/1988 | Fed. Rep. of Germany . |
| 53-134876 | 4/1977 | Japan . |
| 58-029664 | 8/1981 | Japan . |
| 2217335 | 10/1989 | United Kingdom . |

OTHER PUBLICATIONS

"Synthetic Polymeric Membranes" R. E. Kesting, pp. 260-261.

*Primary Examiner*—Frank Sever
*Attorney, Agent, or Firm*—Oliff & Berridge

[57] ABSTRACT

Membranes are based on a homogeneous mixture of polyvinylidene fluoride and a second polymer which can be rendered hydrophilic by chemical reaction. The membranes contain 70 to 98 percent by weight of polyvinylidene fluoride and 2 to 30 percent by weight of a polymer formed essentially from polymethyl and/or polyethyl acrylate, and have a maximum pore size in the range from 0.005 to 10 μm. They can be rendered hydrophilic by means of at least partial hydrolysis, at least partial transesterification with an alcohol which is at least trihydric and contains 3 to 12 carbon atoms, and/or at least partial aminolysis with an amino compound having 2 to 8 carbon atoms. The flat or capillary membranes which have been rendered hydrophilic can contain on their total surface 0.001 to 10 milliequivalents/g of membrane, preferably 0.01 to 5 m equivalents/g of membrane, of —COOH, —OH or —NH$_2$ groups or corresponding mixtures of these hydrophilic functional groups. Such membranes can be used, in particular, for immobilizing biochemically active compounds.

10 Claims, 2 Drawing Sheets

PVDF flat membranes WW 5

Upper side
1000:1

PVDF flat membranes WW 5                    Figure 1

Upper side
1000:1

Upper side
5000:1

ARLO-PA microphotography (scanning electron microscope SEM)
Image width:    secondary electrons    o back-scattered electrons
Preparation: o freeze   fracture         spattered
         with 15 nm Au

PVDF FLAT MEMBRANES WW 6/1

UPPER SIDE
1000:1

UPPER SIDE
5000:1

ARLO-PA MICROPHOTOGRAPHY (SCANNING ELECTRON MICROSCOPE SEM)
IMAGE WIDTH:      SECONDARY ELECTRONS    0   BACK-SCATTERED
ELECTRONS
PREPARATION:  0   FREEZE   FRACTURE      SPATTERED
           WITH 15 nm Au

FLAT OR CAPILLARY MEMBRANE BASED ON A HOMOGENEOUS MIXTURE OF POLYVINYLIDENE FLUORIDE AND A SECOND POLYMER WHICH CAN BE RENDERED HYDROPHILIC BY CHEMICAL REACTION

TECHNICAL FIELD

The invention relates to a flat or capillary membrane based on a homogeneous mixture of polyvinylidene fluoride (PVDF) and a second polymer which can be rendered hydrophilic by chemical reaction, and to processes for their preparation and further chemical modification.

BACKGROUND

Polyvinylidene fluoride membranes which have, in particular, an excellent heat stability and stability towards chemicals are known to be hydrophobic and are difficult to use for separation of aqueous solutions. Numerous attempts to render such membranes hydrophilic by the most diverse types of modification have already been made in the prior art.

German Offenlegungsschrift No. 27 35 887 thus describes a process in which the pores of a porous fluorohydrocarbon polymer are impregnated with at least one water-soluble polymer including polyvinyl alcohol, and the polyvinyl alcohol is rendered insoluble in water by heat treatment or ionizing radiation.

However, impregnation processes have the disadvantage that the membrane structure can become partly blocked by the coating on the membrane pores, which has an adverse influence on the flow values of the membranes. Furthermore, a coating of a hydrophilic polymer on polyvinylidene fluoride is not very stable, especially in the situation of incompatibility of the substrate and coating. It can therefore be destroyed by certain media, in particular sulfuric acid or hypochlorite solutions, which are required for cleaning membranes or in the semiconductor industry, resulting in disadvantages such as increased release of foreign substances or particles, and the hydrophilic character of the membranes is irretrievably lost.

The compatibility of PVDF with hydrophilic polymers is unfortunately very limited. Thus, hydrophilic membranes with a sufficiently high weight content of the hydrophilic component can indeed be prepared from PVDF and a few hydrophilic polymers, such as, for example, polyvinylpyrrolidone. However, they have a very low mechanical strength and the hydrophilic polymer is often extracted from the membrane under use conditions.

PVDF membranes can also be rendered hydrophilic by grafting polymerization. European Patent Application No. 245,000 thus describes a process in which PVDF membranes are first treated with an alkali metal hydroxide solution in order to produce reactive areas on the surface of the PVDF membrane by splitting off hydrogen fluoride Polymerizable hydrophilic vinyl polymers, such as acrylic acid, methacrylic acid and itaconic acid, are then grafted onto these areas using a polymerization initiator. As well as the risk of damage to the membrane by the alkali metal hydroxide solution and blockage of the pores by the polymerized hydrophilic vinyl polymer, this procedure also has the disadvantage that the membrane still contains toxic acrylic monomers and oligomers after the grafting and these can be extracted completely from the membrane only with great expenditure Another way of avoiding the disadvantages described has been disclosed, according to which a membrane is prepared from a homogeneous mixture of PVDF and a second polymer which can be rendered hydrophilic by chemical reaction, which thus must be compatible with PVDF in the weight range used, and the second polymer is then converted into a hydrophilic polymer by chemical reaction. In European Patent Application No. 012,557, a membrane is thus prepared from a homogeneous mixture of PVDF and polyvinyl acetate and the latter is then hydrolyzed, resulting in a hydrophilic membrane which contains hydroxyl groups because of the polyvinyl alcohol formed This patent application emphasizes, however, that the membranes must contain at least 35 percent by weight of polyvinyl acetate if they are to have an adequately hydrophilic character after the hydrolysis has been carried out. A polyvinyl alcohol content of 43 to 67 percent by weight in the hydrophilic membrane is therefore preferred, which corresponds to a polyvinyl acetate weight content originally present of 60–80 percent by weight However, the favorable polymer properties of PVDF described above are of course worsened considerably by such high weight contents of polyvinyl alcohol or polyvinyl acetate.

SUMMARY OF THE INVENTION

The present invention has as an object to provide a membrane based on a homogeneous mixture of PVDF and a second polymer which can be rendered hydrophilic by chemical reaction, and which is distinguished by a considerably lower weight content of the second polymer, which should ensure that on the one hand the outstanding overall chemical and physical properties of PVDF remain virtually intact and on the other hand that adequate hydrophilic properties are nevertheless obtained after this chemical reaction.

Surprisingly, it has been found that the very low weight content of at least 2 percent by weight of a polymer formed essentially from polymethyl and/or polyethyl acrylate is adequate as the second polymer for achieving the stated object. The term "a polymer formed essentially from polymethyl and/or polyethyl acrylate" is understood as meaning, in particular, pure polymethyl acrylate, the corresponding polyethyl acrylate, mixtures of these two polyacrylates and all copolymers of the two monomers methyl acrylate and ethyl acrylate. This furthermore includes copolymers of the last two substances mentioned which are formed by copolymerization of methyl acrylate and/or ethyl acrylate monomers, which have an outstanding capacity for copolymerization, with small amounts of other customary monomers which are known per se. Monomers which are suitable for this and in general can be used only in amounts of up to 10 percent by weight are, for example, acrylamide, acrylonitrile, maleic acid esters, vinyl acetate, vinyl proprionate, methyacrylates, styrene and butadiene. In this connection, it is also surprising that the polymers of methyl and/or ethyl methacrylate or esters of acrylic acid or methacrylic acid with alcohols which contain more than 2 carbon atoms are unsuitable for preparing the membranes according to the invention. Such monomers can at best, as described above, be used as a small admixture, via formation of a copolymer, to the monomers used according to the invention The present invention therefore comprises providing membranes of the type described above, which are comprised of 70 to 98 percent by weight of polyvinylidene fluoride and 2 to 30 percent by weight of a polymer formed essentially from polymethyl and/or polyethyl acrylate, and which have a maximum pore size in the range from 0.005 to 10 μm. Preferred ranges for the maximum pore size are from 0.01 to 2 μm and from 0.05 to 0.8 μm. The maximum pore diameter is determined by means of the blow point method in accordance with ASTM No. 128-61 and F 316-70.

BRIEF DESCRIPTION OF THE FIGURES

FIG. 1A-B shows 1000:and 5000:1 microphotographs of the membrane of Example 1.

DETAILED DESCRIPTION OF THE PREFERRED EMBODIMENTS

Both the average molecular weight of the polyvinylidene and the average molecular weight of the polymer formed essentially from polymethyl and/or polyethyl acrylate can be varied within wide limits. The average molecular weight here is understood as meaning the weight-average $M_w$ measured by gel permeation chromatography after prior calibration with a corresponding standard polymer solution. The polyvinylidene fluoride used for the two processes, described below, according to the invention for the preparation of the membranes can in general have an average molecular weight of 30,000 to 500,000. An average molecular weight of 50,000 to 500,000 is preferred. The average molecular weight of the polymer formed essentially from polymethyl and/or polyethyl acrylate can likewise vary between 5,000 and 1,000,000, although an average molecular weight in the range from 50,000 to 200,000 is preferred for the preparation of the membranes.

Membranes according to the invention can be prepared by preparing a 10 to 40% by weight solution, based on the total weight thereof, of, based on the total polymer weight, 70 to 98 percent by weight of polyvinylidene fluoride and 2 to 30 percent by weight of a polymer formed essentially from polymethyl and/or polyethyl acrylate using one or more solvents and one or more non-solvents. The solution has a range of complete miscibility and a miscibility gap above room temperature in the liquid state and a solidification range above room temperature. The substance components are heated to a temperature above the miscibility gap, while homogeneously mixing intensively. The resulting solution is rapidly cooled from the temperature above the miscibility gap in a cooling liquid and at the same time is shaped to a flat or capillary membrane. The membrane is then freed from residues of solvent and non-solvent by extraction.

This procedure is closely based on the process for the preparation of polyvinylidene fluoride shaped articles containing pores which is described in German Offenlegungsschrift No. 33 29 578, the content thereof being expressly referred to here. To prepare the solution, the polymers are dissolved in a mixture of at least one solvent and at least one non-solvent at elevated temperature, preferably at 200 to 230° C. In the context of the invention, solvents are also to be understood as meaning liquids in which the polymers are insoluble or only very poorly soluble at room temperature but which have good dissolving properties at elevated temperature.

Suitable solvents for the polymers include glycerol triacetate, glycerol diacetate, 2-(2-butoxyethoxy)-ethyl acetate, ε-caprolactam and mixtures of the compounds mentioned. The use of glycerol triacetate as a solvent or a mixture of glycerol triacetate and ε-caprolactam is preferred.

Suitable non-solvents include di-n-octyl adipate or castor oil or a mixture thereof. The homogeneous 10 to 40% by weight thereof prepared at elevated temperature preferably contains, based on the total polymer weight, 80 to 95 percent by weight of polyvinylidene fluoride and 5 to 20 percent by weight of polymethyl and/or polyethyl acrylate. The average molecular weight of the PVDF should preferably be 50,000 to 500,000, and that of the polymethyl and/or polyethyl acrylate should preferably be 50,000 to 200,000.

The abovementioned homogeneous solutions are shaped to a capillary membrane or to a flat membrane and at the same time cooled rapidly, during which they first pass through a range of phase separation. One of the two liquid phases formed after demixing is a polymer-depleted liquid phase of solvents(s) and non-solvent(s), and the other is a polymer-enriched liquid phase depleted in solvent(s) and non-solvent(s). The latter phase leads to solidification of the polymers on further cooling. It is advantageous to use water, if appropriate with added surfactant, as the cooling liquid for the cooling.

However, it is also possible for a liquid or a liquid mixture which gives a clear solution at room temperature or only slightly elevated temperature, that is to say in general in a temperature range from 15 to 50° C, to be used as the solvent. Possible solvents include, in particular, the aprotic solvents. In this case, a 10 to 40% by weight solution, based on the total weight thereof, is preferably prepared from one or more of N-methylpyrrolidone, dimethyl sulfoxide, dioxane, dimethylformamide and dimethylacetamide at a temperature of 0 to 80° C, preferably 20 to 40° C. After shaping as a capillary membrane or as a flat membrane, the solution is precipitated by dipping into a non-solvent, the temperature of the non-solvent bath being 0 to 80° C, preferably 20 to 40° C. Possible non-solvents include all the liquids which do not dissolve the polymers at room temperature and which are miscible with the solvent of the polymer solution at least to a limited degree. Alcohols having 1 to 12 carbon atoms, preferably 1 to 3 carbon atoms, water or mixtures of the substances mentioned are preferred as non-solvents for coagulation of the membrane.

In some cases, it is favorable for the solution to be brought into contact with gaseous non-solvents, such as humid air, steam or vapors of the abovementioned alcohols, for a certain period of time, which can extend from a few seconds to a few minutes, before being brought into contact with the liquid non-solvent. It may also be advantageous to add certain additives to the polymer solution employed for the membrane preparation. Examples of possible additives are thickeners for increasing the viscosity of the polymer solution, nucleating agents for influencing the membrane formation process or dyestuffs or pigments.

The membrane prepared by one of the processes described may be extracted in order to remove residues of solvents and other substances which would interfere during later use of the membrane. Extraction agents which can be employed are all fluids which dissolve the substances to be extracted but not the membrane polymers PVDF, polymethyl acrylate and/or polyethyl acrylate. Lower alcohols having to 3 carbon atoms, in particular isopropanol, are preferably used. The extraction agent is removed from the membrane by drying.

The polymethyl and/or polyethyl acrylates essentially used according to the invention for preparation of the flat or capillary membrane and having an average molecular weight of 5,000 to 1,000,000 are not commercially available. However, they can be synthesized by known processes, even in a solvent, such as triacetin (=glycerol triacetate), N-methylpyrrolidone or dimethylsulfoxide, which is also employed as a solvent in the membrane preparation by adding an amount of to 30 percent by weight of methyl and/or ethyl acrylate and 0.02 to 5 percent by weight, based on the monomers, of a free radical initiator, such as benzoyl peroxide, azobisisobutyronitrile or acetovaleronitrile, to this at room temperature. A corresponding procedure is followed in the copolymerization of methyl and/or ethyl acrylate monomers with small amounts of the monomers mentioned above as examples. The solution is then heated up to 80° C in order to start the polymerization. After the polymerization, unreacted monomers are driven off at elevated temperature and with the aid of an entraining agent, such as water, lower alcohols or ethyl acetate. The solution should no longer contain monomers, so that staff are not at risk from the toxic monomers during membrane preparation and residual content of the monomers in the finished membrane is reliably avoided.

For the membrane preparation described above, according to German Offenlegungsschrift 33 29 578, only the corresponding amounts of non-solvents and polyvinylidene fluoride are then added to the resulting polymethyl and/or polyethyl acrylate solution and the mixture is heated up, while stirring, to achieve a homogeneous solution.

The hydrophobic membrane according to the invention is mechanically stable and stable to heat and has a high chemical stability towards attack by oxidizing agents and acids. Surprisingly, it has a considerably better chemical stability towards sodium hydroxide solution than the hydrophobic PVDF membranes of the prior art. The first discoloration of customary PVDF membranes in 10% strength sodium hydroxide solution at 40° C occurs after 5 minutes, whereas membranes according to the invention show the first signs of discoloration only after between 40 and 60 minutes. The stability of membranes towards alkalis is of great importance in practice in the filtration of basic media or in the cleaning of the membrane with sodium hydroxide solutions.

The hydrophobic membrane according to the invention is surprisingly distinguished by a higher porosity of the outer surface compared with PVDF membranes of the same pore size. Porosity of the outer surface is understood as meaning the area of open pores on the outer surface of the membrane in relation to the area of the outer surface. The porosity of the outer surface is of decisive importance for blockage of a membrane. The greater this porosity of a membrane, the more slowly it becomes blocked when used properly.

The novel hydrophobic membrane is therefore outstandingly suitable for filtration of gases or for applications in which a hydrophilic liquid should not pass through the membrane. Examples of these are gassing of liquids (blood, bioreactors, effluent) or transmembrane distillation.

The hydrophobic membrane according to the invention can be subjected, in particular, to chemical modification over its entire surface, for the purpose of obtaining a hydrophilic membrane, by subjecting the ester groups on the total surface of the membrane to at least partial hydrolysis and/or at least partial transesterification with a polyhydric alcohol and/or at least partial aminolysis with an amino compound having 2-8 carbon atoms. The total surface is understood here as meaning not only the outer surface but also the inner surfaces, that is to say the surfaces of the micropores of the membrane, which come into contact with fluids during their use. The flat or capillary membranes which have been rendered hydrophilic then contain 0.001 to 10 milliequivalents/g of membrane, preferably 0.01 to 5 milliequivalents/g of membrane of $-OH$, $-NH_2$ or $-COOH$ groups or mixtures of these hydrophilic functional groups on their total surface.

The permanent rendering hydrophilic of the membrane according to the invention is so surprising, as already mentioned above, because membranes which also contain, in addition to PVDF, up to 30% by weight of esters of acrylic acid with monohydric alcohols having a carbon atom number higher than 2 or esters of methacrylic acid with monohydric alcohols cannot be rendered hydrophilic by the procedure described.

An only partial hydrolysis or partial transesterification or partial aminolysis of the membrane according to the invention is possible, in particular if the membrane contains comparatively large amounts of polymethyl and/or polyethyl acrylate, for example 10 or by weight. However, partial reactions of the type described are also possible according to the invention if the membrane contains hydrophilic groups but is to remain hydrophobic, or if the membrane which has been rendered hydrophilic is to contain mixtures of the abovementioned hydrophilic functional groups. Any desired sequence of the chemical reactions in question can be chosen for this purpose.

As regards the feasibility of the chemical reactions in question, it is assumed that the polyacrylate macromolecules are distributed randomly in the PVDF. Portions of macromolecules of the polymethyl and/or polyethyl acrylate are thus to be encountered individually over the total surface inside the pores of the membrane. At least some of the ester groups of these macromolecule portions can be converted into $-OH$, $-NH_2$ or $-COOH$ groups by the chemical reactions in question, whereas the corresponding portions of polyacrylate macromolecules inside the membrane can undergo no chemical reaction. These therefore remain anchored in the membrane structure and cannot be washed out. On the other hand, the hydrophilic functional groups in the macromolecule portions of the acrylic acid polymer present on the outer and inner surfaces of the membrane render the membrane permanently hydrophilic.

The hydrolysis of the membrane according to the invention can be carried out by treating the ester groups on the total surface of the membrane with concentrated sulfuric acid at a temperature of 40 to 80° C for 1 to 20 hours. The rate of hydrolysis here increases as the temperature increases. Although other strong acids, such as hydrochloric acid, methanesulfonic acid and perchloric acid, can be used for the hydrolysis, treatment of the membrane with concentrated sulfuric acid is preferred in the context of the invention. So that the membrane can be wetted during this treatment and the increase in temperature due to the heat of dilution of the sulfuric acid can be kept sufficiently low, it may be advantageous to dip the membrane into the following solutions, for example, in succession: $C_1$-$C_4$-alcohol - water - 50% $H_2SO_4$ - 70% $H_2SO_4$ - 98% $H_2SO_4$ - 70% $H_2SO_4$ 50% $H_2SO_4$ - water.

In the present case, the hydrolysis can also be carried out under basic conditions. However, it should be remembered here that the pH of the reaction medium should be less than 11, since otherwise the polyvinylidene fluoride will be attacked. For this purpose, it is advantageous to carry out the reaction in the presence of a buffer solution, for which an aqueous borax solution which is saturated at room temperature has proved to be particularly suitable. Since the basic hydrolysis is also relatively protracted, it is advantageously carried out in a pressure vessel at a temperature of 80 to 140° C and a pH of 9 to 11.

The membrane according to the invention can also be rendered hydrophilic by providing it with alcoholic OH groups on its total surface by means of transesterification (=alcoholysis). For this purpose, the ester groups on the total surface of the membrane are subjected to at least partial transesterification with an alcohol which is at least trihydric, with the addition of 0.1 to 10% by weight, based on the polyhydric alcohol, of a strong acid, at a temperature of 100 to 150° C. for 5 to 30 hours. Examples of strong acids which can be used here include sulfuric acid, hydrochloric acid, methanesulfonic acid and perchloric acid.

Suitable polyhydric alcohols are alcohols containing three or more OH groups, such as glycerol, diglycerol, triglycerol, polyglycerol mixtures, trimethylolethane, trimethylolpropane, pentaerythritol, dipentaerythritol, tripentaerythritol, butane-1,2,4-triol, hexanetriol, sugar-alcohols, such as sorbitol and mannitol, and monosaccharides, such as fructose and mannose. Mixtures of polyhydric alcohols can of course also be used. One or more compounds from the group comprising glycerol, diglycerol, triglycerol, a polyglycerol mixture, pentaerythritol and sorbitol are preferably used as the polyhydric alcohol.

An analogous treatment of the membrane in ethylene glycol or low molecular weight polyethylene glycols astonishingly does not lead to the membrane surface being rendered hydrophilic. However, ethylene glycol can advantageously be used as the reaction medium for the alcoholysis, in order to dissolve the solid substances which are possible, such as pentaerythritol and the monosaccharides, and to react them with the membrane.

Aminolysis is another procedure for rendering hydrophilic the membrane according to the invention. Since primary and secondary amines attack polyvinylidene fluoride at elevated temperature because of their basicity, the reaction conditions, such as pH, temperature and reaction time, should be adapted to these circumstances. It has proved advantageous for the ester groups on the total surface of the membrane to be subjected to at least partial aminolysis with at least one amino compound having 2 to 8 carbon atoms using corresponding buffer mixtures at a pH of 11 and a temperature of 50 to 150° C. for 1 to 24 hours. In the simplest case, the solution of the corresponding amino compound can be buffered to saturation with ammonium chloride.

Amino compound in the sense of the invention is understood here as meaning organic compounds having 2 to 8 carbon atoms and one or more primary amino groups, with the proviso that if only one primary amino group is present, at least two other hydrophilic functional groups are present in the form of hydroxyl and-/or carboxyl groups. Examples of these compounds include 1,2-diaminoethane, 1,2-diaminopropane, 1,3-diaminopropane, 1,4-diaminobutane, 1,3-diaminobutane, 1,2-diaminobutane, 1,8-diaminooctane, aspartic acid, glutamic acid and homoserine.

Also included here are, in particular, primary and secondary polyamines having two primary amino groups and amines having 3 primary amino groups, specific urea derivatives and heterocyclic hydrazines containing several hydrazine radicals. As in the case of the alcoholysis described above, the conversion, according to the invention, of the hydrophobic membrane into a hydrophilic membrane requires only the presence of comparatively low amounts by weight of polymethyl and/or polyethyl acrylate in the flat or capillary membrane, because of the higher number of hydrophilic groups per molecule, which benefits the use properties of the hydrophilic membrane. Examples of these polyamines are diethylenetriamine, triethylenetetramine, tetraethylenepentamine, dipropylenetriamine, 1,2,3-triaminopropane, 2,4,6-triamino-1,3,5-triazine, 2,4,6-trihydrazin-1,3,5-triazine, isobutylidenediurea, biuret and triuret. Mixtures of amino compounds which can be used can of course also be employed. It is preferable for one or more compounds from the group comprising diethylenetriamine, triethylenetetramine and tetraethylenepentamine to be used as the amino compound.

Surprisingly, it has been found that the flat or capillary membranes rendered hydrophilic in the manner described above also have a considerably better chemical stability towards sodium hydroxide solution than the hydrophobic PVDF membranes of the prior art. Whereas the first discoloration of customary PVDF membranes in 10% strength sodium hydroxide solution at 40° C. occurs after 5 minutes, the membranes which have been rendered hydrophilic according to the invention show the first discoloration phenomena only after 45 minutes. This surprising property therefore allows extreme use conditions when using the hydrophilic flat or capillary membrane according to the invention for immobilizing biochemically active compounds, which are excluded in the case of the hydrophilic membranes of the prior art. Biochemically active compounds here are understood as meaning substrates, inhibitors and coenzymes of enzymes and analogs thereof, enzymes themselves, other proteins, other cell constituents, whole cells or compounds produced by cells, as well as compounds which can interact in any way with the substance groups listed, that is to say also with whole cells.

The hydrophilic membranes of the invention may contain OH, $NH_2$ or COOH end groups or mixtures of these hydrophilic functional end groups. Such membranes can advantageously be reacted with biochemically active compounds. Such reactions can include reactions of $NH_2$ groups with aldehydes, reactive carboxylic acid derivatives and alkyl or aryl halides, of OH groups with reactive carboxylic acid derivatives and alkyl or aryl halides and of (activated) COOH groups with amines, alcohols and alkyl or aryl halides as the first step. A number of such reactions are described, for example, in German Patent No. 28 28 194 for derivatization of a matrix based on polysaccharide. Because of the complexity of this field, however, the reactions listed here and in DE 28 28 194 cannot be comprehensive. A suitable chemical reaction is always to be matched to suit the individual case to be processed, since the nature of the processed biologically active compounds can vary considerably and the nature of the matrix can also have an influence on the result. When such reactions are carried out on the hydrophilic membrane according to the invention, an activated membrane is obtained which in turn can easily react with other molecules containing functional groups. A membrane to which a biochemically active molecule, a cell constituent or a cell is bonded is called a derivatized membrane here.

The biochemically active compound can sometimes be immobilized directly on the membrane or, if, for example, steric hindrances do not allow this, also after intermediate positioning of one or more spacers. A spacer here is understood as being a molecule which contains at least two functional groups, for example in the form of an aldehyde group, amino group, carboxyl group or hydroxyl group, and acts as a permanent "distancer".

The use according to the invention of the hydrophilic flat or capillary membrane for immobilizing biochemically active compounds leads to a derivatized membrane which can be used, inter alia, as a medium for a combination of filtration and affinity chromatography. Substrate(s), coenzyme(s), inhibitor(s), antibodies and/or analogs thereof, for example, can be employed as covalently bonded ligands for this purpose. The chemically active membrane is furthermore suitable for immobilizing enzymes, other proteins, cell constituents and/or whole cells. The advantage of a filtration unit is combined here with those of immobilizations known from the literature.

The derivatized membranes in question have the particularly advantageous property of having a basic structure which is extremely stable chemically and physically and is in general hydrophilic. This is a decisive advantage in particular for chemical activation under drastic conditions (extreme pH values, elevated temperatures, aggressive solvents). The following surprising effect is moreover established when cleaning a spent derivatized membrane. As described in Example 24, when ligands which are relatively stable chemically are used, cleaning can be carried out considerably faster and more effectively than, for example, in the case of the known carrier materials of a cellulosic nature not only with strong acids but also with strong alkalis, without degradation of the membrane or ligand taking place. Such a procedure would be inconceivable with the known membranes based on cellulose, since they would suffer very great damage or be destroyed under these conditions.

A somewhat less stable bond between the membrane and the ligand can furthermore even be split under correspondingly drastic conditions, as mentioned, for example, in Examples 10, 16 and 23, and the membrane is thus returned to its original hydrophilic state. The membrane can thus be used several times for immobilizing biochemically active compounds, which has not hitherto been described for a derivatizable membrane. This is of particular advantage for immobilizing enzymes having a short life.

The present invention is illustrated in more detail with the aid of the following examples:

A. Preparation of the polyacrylic acid esters $A_1$: Preparation of polymethyl acrylate (=PMA), Mw=7,400

1,800 g of triacetin are initially introduced at 70° C. into a 4 liter glass flask which can be heated. A stream of nitrogen is passed through the liquid for about 0.5 hour to remove oxygen.

4 percent by weight of acetovaleronitrile are dissolved in 200 g of methyl acrylate (MA) at room temperature. This solution is added dropwise to the glass flask containing the triacetin in the course of one hour. Half an hour after the end of the addition, the reaction mixture is heated at 160° C. for half an hour for substantial reaction of residual monomers. Thereafter, the last residues of monomers are removed from the solution by distillation of about 10μg of triacetin. A viscous solution of polymethyl acrylate (PMA) in triacetin remains. The average molecular weight was 7,400.

$A_2$: Preparation of PMA, Mw=35,000

1,400 g of triacetin (=glycerol triacetate) are initially introduced at 70° C. into a 4 liter glass flask which can be heated. A stream of nitrogen is passed through the liquid for about 0.5 hour to remove oxygen.

5 percent by weight of benzoyl peroxide are dissolved in 600 g of methyl acrylate (MA) at room temperature. This solution is added dropwise to the glass flask containing the triacetin in the course of one hour. Half an hour after the end of the addition, the reaction mixture is heated at 160° C. for half an hour for substantial reaction of residual monomers. Thereafter, the last residues of monomers are removed from the solution by distillation of about 100 g of triacetin. A viscous solution of polymethyl acrylate (PMA) in triacetin reactive remains. The average molecular weight $M_w$ (weight-average) was 35,000.

$A_3$: Preparation of PMA, $M_w$=230,000

1,400 g of triacetin are initially introduced at 70° C. into a 4 liter glass flask which can be heated. A stream of nitrogen is passed through the liquid for about 0.5 hour to remove oxygen.

3 percent by weight of benzoyl peroxide are dissolved in 600 g of methyl acrylate (MA) at room temperature. This solution is added dropwise to the glass flask containing the triacetin in the course of one hour. Half an hour after the end of the addition, the reaction mixture is heated at 160° C. for half an hour for substantial reaction of residual monomers. Thereafter, the last residues of monomers are removed from the solution by distillation of about 100 g of triacetin. A viscous solution of polymethyl acrylate (PMA) in triacetin remains. The average molecular weight was 230,000.

$A_4$: Preparation of PMA, $M_w$=688,000

0.5 percent by weight of acetovaleronitrile is dissolved in 20 g of methyl acrylate (MA) at room temperature. This solution is heated to 80° C. in a glass flask in the course of one hour. After another half an hour, the reaction mixture is heated at 160° C. for half an hour for substantial reaction of residual monomers. After cooling, a rubber-like clear polymer is obtained. The average molecular weight was 688,000.

A₅: Preparation of polyethyl acrylate (=PEA), $M_w$=114,000

1600 g of triacetin are initially introduced at 70° C. into a 4 liter glass flask which can be heated. A stream of nitrogen is passed through the liquid for about 0.5 hour to remove oxygen.

0.2 percent by weight of benzoyl peroxide is dissolved in 400 g of ethyl acrylate (EA) at room temperature. This solution is added dropwise to the glass flask containing the triacetin in the course of one hour. Half an hour after the end of the addition, the reaction mixture is heated at 160° C. for half an hour for substantial reaction of residual monomers. Thereafter, the last residues of monomers are removed from the solution by distillation of about 100 g of triacetin. A viscous solution of polyethyl acrylate (PEA) in triacetin remains. The average molecular weight $M_w$ was 114,000.

A₆: Preparation of pMA/pEA, $M_w$=160,000

800 g of triacetin are initially introduced at 70° C. into a 2 liter glass flask which can be heated. A stream of nitrogen is passed through the liquid for about 0.5 hour to remove oxygen.

0.2 percent by weight of benzoyl peroxide is dissolved in 150 g of methyl acrylate (MA) and 150 g of ethyl acrylate (EA) at room temperature. This solution is added dropwise to the glass flask containing the triacetin in the course of one hour. Half an hour after the end of the addition, the reaction mixture is heated at 160° C. for half an hour for substantial reaction of residual monomers. Thereafter, the last residues of monomers are removed from the solution by distillation of about 100 g of triacetin. A viscous solution of a copolymer of methyl acrylate (MA) and ethyl acrylate (EA) in triacetin remains. The average molecular weight $M_w$ was 160,000.

B. Preparation of flat or capillary membranes according to the invention

EXAMPLE 1

Preparation of a PVDF/PMA flat membrane.

27 parts (always parts by weight) of PVDF of the type Kynar 460 (Pennwalt), 3 parts of polymethyl acrylate (A₁), 18.2 parts of triacetin, 4.55 parts of ε-caprolactam and 47.25 parts of dioctyl adipate were brought together in a glass flask with a stirrer. The PVDF employed in this and the other examples, with the exception of Example 2, has, unless stated otherwise, an average molecular weight of 361,000 according to gel permeation chromatography. The mixture was heated up to 240° C., while stirring, until a homogeneous solution was obtained. The solution was then cooled to 190° C. This solution was shaped to a film on a casting roll, which was temperature-controlled at 20° C., with the aid of a casting box and the film was wound up on a roll. Samples of the films were extracted in isopropanol at 60° C. three times for 0.5 hour for substantial washing out of the solvents from the membrane. After drying, a white flat membrane was obtained.

The membrane thickness is 120 μm and the maximum pore size of the membrane is 0.55 μm. The flow of isopropanol through the membrane is 7.4 ml/(cm² minute bar).

No flow of water takes place through the membrane under a transmembrane pressure of 0.5 bar.

Figure 1:
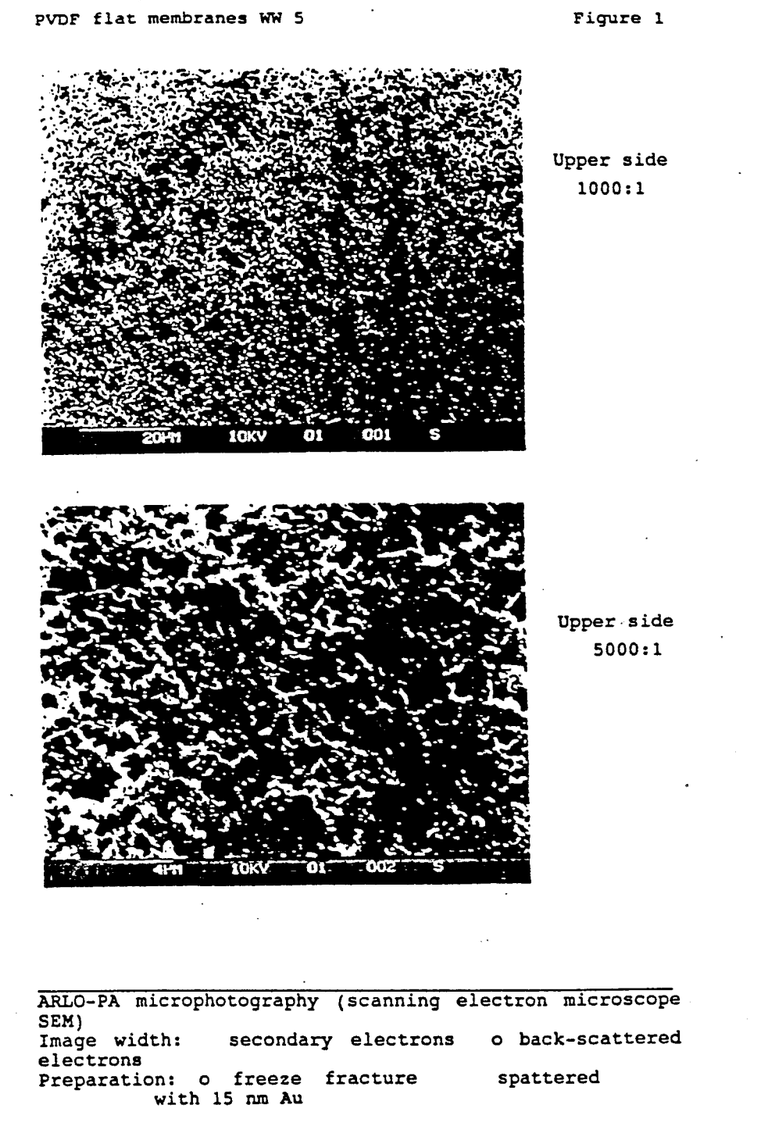

The surfaces of the flat membrane are very open-pored (see the microphotographs, FIG. 1).

EXAMPLE 2:

Preparation of a PVDF/PMA flat membrane having a low $M_w$ of PVDF 56 g of PVDF of the type Kynar 740 (Pennwalt) ($M_w$=180,000), 132 g of dioctyl adipate, 12 g of triacetin and 75 g of a 20 percent strength solution of polyethyl acrylate (A₅) in triacetin were brought together in a glass flask with a stirrer. The mixture was heated up to 240° C., while stirring, until a homogeneous solution was obtained. This solution was knife-coated onto a glass plate to give a film of 200 μm layer thickness. The film was solidified by dipping into water. The film was extracted in isopropanol at 60° C. three times for 0.5 hour for substantial washing out of the solvents from the membrane. After drying, a white flat membrane was obtained.

EXAMPLE 3:

Preparation of PVDF/PMA capillary membranes having very small pores.

A solution, prepared analogously to Example 1, of 32.5 parts of PVDF of the type Kynar 460, 2.5 parts of PMA (A₂), 22.75 parts of triacetin and 42.25 parts of dioctyl adipate was spun through an annular die at a temperature of 205° C. to give a capillary membrane. Glycerol was conveyed through a hollow needle inside the annular die to keep the capillary cavity open.

The membrane was extracted in isopropanol at 60° C three times for half an hour.

The capillary membrane had an internal diameter of 0.2 mm and an external diameter of 0.29 mm.

The maximum pore size of the membrane was less than about 0.2 μm and thus cannot be determined by the blow point method. The flow of isopropanol through the membrane was 0.15 ml/(cm² minute bar).

The separation properties of the membrane were measured by determination of the sieve coefficients for various macromolecules. The sieve coefficient is defined as the quotient of the concentration of the macromolecules in the solution as passing through the member divided by the concentration of the macromolecules in the original test solution passing through the membrane.

The following values were obtained for the sieve coefficients:

| Macromolecule | Molecular weight | Sieve coefficient |
| --- | --- | --- |
| Vitamin B12 | 1,300 | 0.87 |
| Inulin | 5,500 | 0.79 |
| Cytochrome C | 12,000 | 0.54 |
| α-Amylase | 45,000 | 0.24 |
| Bovine serum albumin | 60,000 | 0.16 |

This means that molecules having a molecular weight of 45,000, which corresponds to a molecule diameter of 0.03 μm, are almost completely retained by the membrane.

EXAMPLE 4

Comparison example: Preparation of a PVDF flat membrane.

27.5 parts of PVDF of the type Kynar 460 (Pennwalt), 18.85 parts of triacetin, 4.71 parts of ε-caprolactam and 48.94 parts of dioctyl adipate were brought together in a glass flask with a stirrer. The mixture was heated up to 240° C., while stirring, until a homogeneous solution was obtained. The solution was then cooled to 190° C. This solution was shaped to a film on a casting roll, which was temperature-controlled at 20° C., with the aid of a casting box and the film was wound up on a roll. Samples of the films were extracted in isopropanol at 60° C. three times for 0.5 hour for substantial washing out of the solvents from the membrane. After drying, a white flat membrane was obtained.

The membrane thickness is 140 μm and the maximum pore size of the membrane is 0.59 μm. The flow of isopropanol through the membrane is 9.4 ml/(cm² minute bar).

No flow of water takes place through the membrane under a transmembrane pressure of 0.5 bar.

Figure 2A:
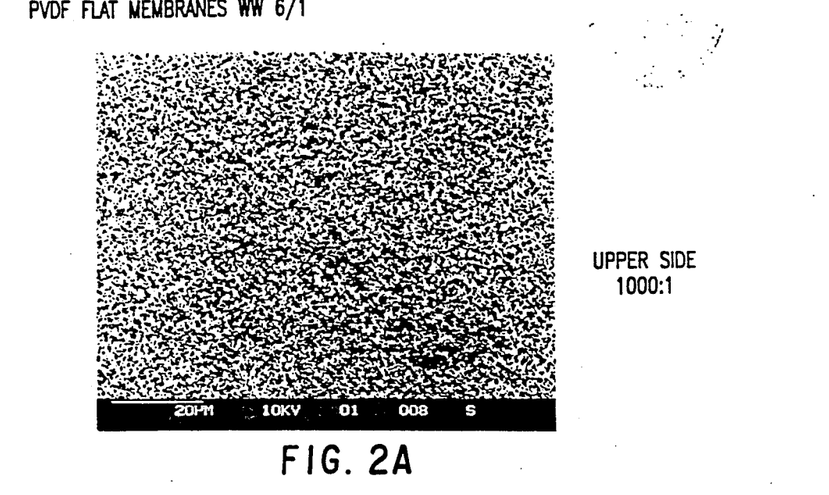
FIG. 2 shows 1000:1 and 5000:1 microphotographs of the membrane of Example 4.
Figure 2B:
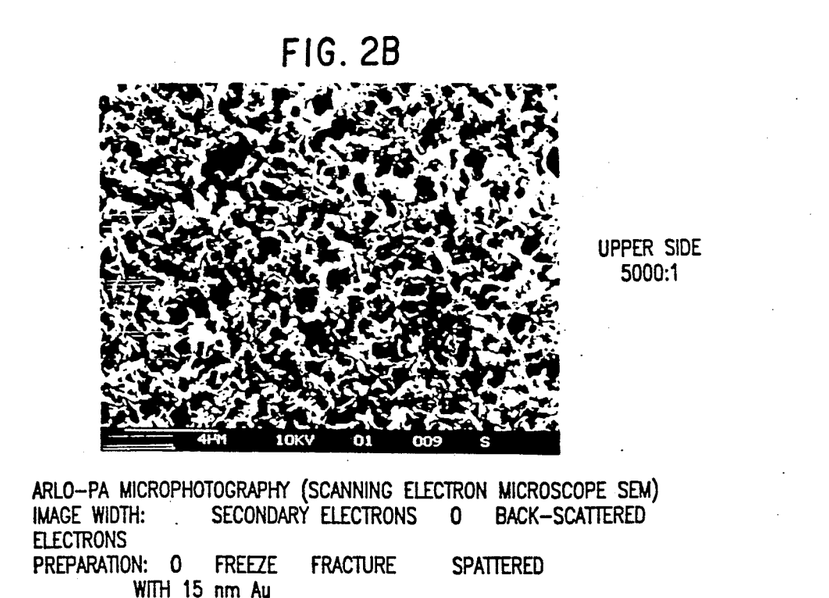

The surfaces of the membrane ar less open-pored than in Example 1 (see the microphotographs, FIG. 2).

EXAMPLE 5

Preparation of a PVDF/PEA flat membrane.

56 g of PVDF of the type Kynar 460 (Pennwalt), 132 g of dioctyl adipate, 12 g of triacetin and 75 g of a 20 percent strength by weight solution of polyethyl acrylate ($A_5$) in triacetin were brought together in a glass flask with a stirrer. The mixture was heated up to 240° C., while stirring, until a homogeneous solution was obtained. This solution was knife-coated onto a glass plate to give a film of 200 μm layer thickness. The film was solidified by dipping into water. The film was extracted in isopropanol at 60° C. three times for 0.5 hour for substantial washing out of the solvents from the membrane. After drying, a white flat membrane was obtained. The maximum pore diameter was 0.82 μm and the flow of isopropanol was 9.1 ml/(cm² minute bar).

EXAMPLE 6

Preparation of a PVDF/PMA/PEA flat membrane 135 g of PVDF of the type Kynar 460 (Pennwalt), 303.8 g of dioctyl adipate, 29.2 g of ε-caprolactam, 117 g of triacetin and 10 g of polymethyl/ethyl acrylate ($A_6$) were brought together in a glass flask with a stirrer. The mixture was heated up to 240° C., while stirring, until a homogeneous solution was obtained. This solution was cooled to 195° C. and knife-coated onto a glass plate to give a film of 200 μm layer thickness. The film was solidified by dipping into water. The film was extracted in isopropanol at 60° C. three times for 0.5 hour for substantial washing out of the solvents from the membrane. After drying, a white flat membrane was obtained. The maximum pore diameter was 0.86 μm and the flow of isopropanol was 9.4 ml/(cm² minute bar).

EXAMPLE 7

Preparation of a PVDF/PMA flat membrane using DMSO as the solvent 54 g of PVDF of the type Kynar 460 (Pennwalt) and a solution of 6 g of polymethyl acrylate ($A_3$) in 340 g of dimethyl sulfoxide (DMSO) were brought together in a glass flask with a stirrer. The mixture was heated up to 80° C., while stirring, until a homogeneous solution was obtained. 100 g of propylene carbonate were added to the solution. This solution was cooled to room temperature without phase separation taking place. The solution was knife-coated onto a glass plate to give a film of 200 μm layer thickness. The film was first kept in air for one minute and then solidified by dipping into water.

The film was extracted in isopropanol at 60° C. three times for 0.5 hour for substantial washing out of the solvents from the membrane. After drying, a white flat membrane was obtained.

The maximum pore size of the membrane is 2.46 μm and the flow of isopropanol through the membrane is 11.2 ml/(cm² minute bar).

The membrane was treated with diglycerol and 2% strength sulfuric acid in accordance with Example 16. The penetration time (see Example 10) of the membrane treated in this way was 12 seconds.

EXAMPLE 8

Preparation of PVDF/PMA capillary membranes

A solution, prepared as in Example 1, of 31.1 parts of PVDF, 2.9 parts of PMA ($A_4$), 22.44 parts of triacetin, 4.29 parts of ε-caprolactam and 44.55 parts of dioctyl adipate was spun through an annular die at a temperature of 210° C. to give a capillary membrane. A mixture of equal parts of castor oil and dioctyl adipate was conveyed through a hollow needle inside the annular die to keep the capillary cavity open.

The membrane was extracted in isopropanol at 60° C. three times for half an hour. The extracted membrane has a maximum pore size of 0.63 μm and an isopropanol flow of 9.24 ml/(cm² minute bar). The capillary membrane has an internal diameter of 1.0 mm and an external diameter of 1.5 mm.

The membrane cannot be wetted with water.

EXAMPLE 9

Preparation of a PVDF capillary membrane

A PVDF solution consisting of 29.9 parts of PVDF, 18.2 parts of triacetin, 4.6 parts of ε-caprolactam and 47.3 parts of dioctyl adipate was spun to a capillary membrane, without addition of a polyacrylate, in accordance with Example 8.

The membrane was extracted in isopropanol at 60° C. three times for half an hour. The extracted membrane has a maximum pore size of 0.54 μm and an isopropanol flow of 6.55 ml/(cm² minute bar).

The membrane cannot be wetted with water. The capillary membrane has an internal diameter of 1.0 mm and an external diameter of 1.5 mm.

EXAMPLE 10

Reaction of PVDF/PEA with $H_2SO_4$

Samples of the membrane according to Example 5 were reacted with sulfuric acid.

For this, the membranes were first wetted with ethanol. The membranes were then brought into contact with concentrated sulfuric acid, without incorporating gas bubbles into the membrane structure, by replacing the alcohol with demineralized water, then with 70 percent sulfuric acid and then with concentrated sulfuric acid (98%). The membranes remained in the sulfuric acid at 60° C. for 1.5 hours.

Thereafter, the membranes were washed out first with 70 percent sulfuric acid and then with demineralized water and subsequently dried. The dry samples were hydrophilic.

The penetration time was about 30 seconds.

Penetration time in this and in the following examples is understood as meaning the time after which a drop of water of 2 μl applied to the membrane with a precision pipette has disappeared completely. The time of more than about 300 seconds which the drop of water requires to disappear completely by evaporation on a glass rod is used for comparison. In the case of a hydrophilic membrane, it takes less time, of course, before the drop of water has disappeared, since it is absorbed by the membrane structure. Because the membrane structure is not always the same, which also influences the penetration times, determination of the penetration time offers a measure, which is only semi-quantitative but adequate and above all close to conditions in practice, of the hydrophilicity of a membrane, since use of the membrane in practice depends on complete wetting of the membrane with water within a certain time.

EXAMPLE 11

Reaction of PVDF/PMA with borax solution

A sample of the flat membrane according to Example 5 was wetted with isopropanol and then treated in 5 percent by weight sodium hydroxide solution, which was saturated with borax, in a pressure vessel at 120° C. for 8 hours. The membrane was then rinsed out with demineralized water and dried. The membrane was slightly brownish and hydrophilic. The penetration time was about 40 seconds.

EXAMPLE 12

Reaction with glycerol and diglycerol

Capillary membranes which were prepared analogously to Examples 8 and 9 and had a different content of PMA, based on the polymer, were treated with glycerol and diglycerol respectively as a solution for rendering them hydrophilic. The treatment time was in each case 6 hours at 140° C. 1% by weight of perchloric acid was added to the solution for rendering the membranes hydrophilic.

In this procedure, the membrane samples were first wetted with ethanol and then dipped into the particular solution for rendering them hydrophilic. After the treatment, the membranes were washed with demineralized water and dried. The penetration times were determined on the dry membrane samples.

| Membrane: PVDF and | Penetration times in seconds | | |
|---|---|---|---|
| | Glycerol | Diglycerol | Diglycerol + 10% of water |
| 0% of PMA | >300 | >300 | >300 |
| 13.5% of PMA | 1-2 | 1 | 1 |
| 8.5% of PMA | 2-3 | 2-3 | 1-2 |

EXAMPLE 13

Transesterification of PVDF/PMA/PEA with diglycerol

A membrane according to Example 6 was added to a solution of diglycerol and 6% by weight of concentrated sulfuric acid (98%), after prewetting with ethanol. The solution was kept at 140° C. for 8 hours. The membranes were then taken out, extracted several times with demineralized water and dried.

The penetration time on the dry membrane was 2-3 seconds.

EXAMPLE 14

Transesterification of PVDF with 2% of PMA

A flat membrane which had been prepared from PVDF and 2% of PMA analogously to Example 5 was treated with diglycerol and 2% by weight of concentrated sulfuric acid at 140° C. for 20 hours, as in Example 13. After the membrane had been washed out and dried, the penetration time was 70 seconds.

EXAMPLE 15

Transesterification of PVDF/PMA with various alcohols

Membrane samples which had been prepared according to Example 8 were wetted with methanol and reacted with various alcohols at 140° C. for 6 hours, 1% by weight of perchloric acid being added:

| Alcohol | Penetration time (seconds) |
|---|---|
| Glycerol | 3 |
| Diglycerol | 1 |
| Polyglycerol | 2 |
| Ethylene glycol | >300 |
| Polyethylene glycol 300 | >300 |
| 10% by weight of alcohol in ethylene glycol: | |
| Sorbitol | 2 |
| Sucrose | 2 |
| Starch | >300 |
| Pentaerythritol | 3 |
| TRIS | 60 |

TRIS = tris(hydroxymethyl)aminomethane

EXAMPLE 6

Transesterification of PVDF/PMA flat membranes with diglycerol and various acids Membrane samples according to Example 1 were reacted with a solution of diglycerol and in each case 4 different concentrated acids. The treatment lasted 8 hours at 140° C. The penetration times of the rinsed and dried membranes are stated.

| Acid | Penetration time (seconds) |
|---|---|
| Hydrochloric acid (35%) | 8 |
| Perchloric acid (70%) | 2 |
| Sulfuric acid (98%) | 2 |
| Phosphoric acid (85%) | >300 |

In contrast to the membranes from Examples 1 and 4, the hydrophilic membrane samples according to Example 16 have a water flow of about 7.4 ml/(cm² minute bar) under a transmembrane pressure of 0.5 bar.

EXAMPLE 17

Determination of the hydroxyl groups

The hydroxyl number was determined on the membrane from Example 16, which had been rendered hydrophilic with diglycerol/sulfuric acid, as a measure of the amount of free OH groups on the membrane surface.

For this, the membrane was reacted with an acetylation mixture. The amount consumed is determined by back-titration of the solution. Preparation of the acetylation mixture:

3.5 ml of perchloric acid (70%) are brought together with 150 ml of ethyl acetate and 5 ml of acetic anhydride. One part of hexane is added to 4 parts of the solution.

Measurement

A weighed piece of membrane was introduced into a conical flask, and 5 ml of acetylation mixture and 2 ml of water were added. After 5 minutes, 25 ml of a mixture of 3 parts of pyridine and 1 part of water were added. After a further 5 minutes, the mixture was diluted with 50 ml of isopropanol and titrated with 1 normal sodium hydroxide solution, using phenolphthalein as the indicator.

The content of OH groups was determined as 0.3 m equivalents/g.

EXAMPLE 8

Preparation of a hydrophilic comparison membrane according to German Offenlegungsschrift No. 27 35 887

A hydrophobic capillary membrane of PVDF (according to Example 9) was dipped into an aqueous solution containing 6% by weight of polyvinyl alcohol analogously to Example 29 of DE-OS 27 35 887. The membrane was dried and then treated at 90° C. for 20 minutes and at 140° C. for 5 minutes. The membrane was rinsed with water at 90° C. twice for 10 minutes. The dried membrane was dipped into an acetalizing bath of 20 parts of sulfuric acid (96%), 2 parts of sodium sulfate and 100 parts of a 40% by weight solution of formaldehyde in water at room temperature for 2 minutes. The membranes were then rinsed with water and dried.

EXAMPLE 19

Treatment of hydrophilic membranes with hypochlorite solution

A capillary membrane according to Example 12 containing 8.5% by weight of PMA and with glycerol treatment and the comparison membrane according to Example 16 were kept in an aqueous solution containing 5000 ppm of sodium hypochlorite for 16 hours and then rinsed with water and dried. The membrane according to the invention still had good hydrophilic properties, whereas the comparison membrane was no longer wetted by water, as can be seen from the comparison of the penetration times.

| Membrane | Penetration time (seconds) |
|---|---|
| According to Example 10 | 15 |
| According to Example 16 | >300 |

EXAMPLE 20

Comparison with a hydrophilic PVDF membrane from Millipore

A commercially available hydrophilic flat membrane of PVDF from Millipore and a PVDF flat membrane according to the invention, which had been rendered hydrophilic according to Example 16 by treatment with sulfuric acid and diglycerol, were kept in concentrated sulfuric acid for 16 hours. The membranes were then rinsed with water and dried.

The membrane according to the invention still had good hydrophilic properties, whereas the comparison membrane was no longer wetted by water, as can be seen from the comparison of the penetration times.

| Membrane | Penetration time (seconds) |
|---|---|
| According to Example 16 | 12 |
| Millipore | >300 |

EXAMPLE 21

Treatment of a PVDF/PMA capillary membrane according to Example 8 with tetraethylenepentamine A reaction solution was prepared by saturating an aqueous solution containing 40% by weight of tetraethylenepentamine with ammonium chloride at 80° C. A capillary membrane according to Example 8 was wetted with ethanol and then dipped into the solution at 80° C. After the ethanol had evaporated, the solution containing the membrane was heated up to 140° C. in a pressure vessel. Membrane samples were taken out of the solution after various times, washed with water and dried. The membranes were only slightly discolored, and after a reaction time of more than 3 hours were still readily wettable with water.

| Reaction time (hours) | Penetration time (seconds) |
|---|---|
| 1 | >300 |
| 3 | >300 |
| 5 | 26 |
| 7 | 2 |
| 16 | 2 |

A comparison membrane according to Example 9 without added polyacrylate treated in the same manner showed no hydrophilicity even after a reaction time of 16 hours.

EXAMPLE 22

Treatment of a PVDF/PMA capillary membrane according to Example 8 with glutamic acid A reaction solution was prepared by buffering an aqueous solution of 40% by weight of glutamic acid to pH 10 with ammonia. A capillary membrane according to Example 8 was wetted with ethanol and then dipped into the solution at 80° C. After the ethanol had evaporated, the solution containing the membrane was heated up to 140° C. in a pressure vessel. The membrane was taken out of the solution after 16 hours, washed with water and dried.

The membrane had a penetration time of 18 seconds. A comparison membrane according to Example 9 which had been treated in the same manner could not be wetted with water and thus showed a penetration time of >300 seconds.

EXAMPLE 23

Stability toward sodium hydroxide solution

One flat membrane each according to Example 1 and Example 4 and a hydrophilic flat membrane, transesterified with diglycerol, according to Example 15 were wetted with methanol and placed in 10% by weight sodium hydroxide solution at 40° C. The time until the first discoloration of the membrane samples occurred was measured.

A discoloration of the membrane indicates a chemical change to the membrane by attack by sodium hydroxide solution.

| Membrane | Time taken for the first discoloration |
|---|---|
| Example 1 | 50 minutes |
| Example 4 | 5 minutes |
| Hydrophilic membrane according to Example 15 | 45 minutes |

EXAMPLE 24

Affinity chromatography with a chemically stable ligand a) Membrane with Cibacron Blue
Hollow fiber membrane data:

| | |
|---|---|
| Internal diameter: | 960–1120 μm; |
| Wall: | 230 μm; |
| PVDF: | 90.5% by weight; |
| PMA: | 9.5% by weight |
| Content of OH groups: | 0.012 milliequivalent/g of membrane, obtained according to Example 12 by reaction of a capillary membrane containing 8.5% of PMA with glycerol |
| Maximum pore diameter: | 0.79 μm |
| Transmembrane flow of isopropanol: | 19.4 ml/(cm² minute bar) |
| Module data: | effective length 155 mm; 62 fibers (5.6 g; 314 cm² internal wall area) |

Pretreatment: The membrane is activated by pumping the corresponding solutions in circulation through the membrane. The membrane is treated with 300 mg of Cibacron Blue 3GA in 60 ml of water for 45 minutes. Solid NaCl is then added to saturation and the membrane is treated for a further 30 minutes. The membrane is then heated to 80° C., 600 mg of $NaCO_3$ are added and the membrane is left at this temperature for a further 2 hours. After cooling, it is washed with 2 liters of water in a single pass.

b) Chromatography
I. Purification of hexokinase

A crude preparation of hexokinase (from yeast, Sigma Order No. H 5!25) is dissolved in 50 ml of 5 mM (millimolar) TRIS-HCl buffer pH 6.4 and the solution is filtered through the membrane. 2×50 ml of the same buffer are used for washing. Elution is carried out with 50 ml of 20 mM TRIS-HCl buffer pH 8.6. The results are shown in Table 1

TABLE 1

| | Hexokinase: | | |
|---|---|---|---|
| | Activity [IU]* | Protein [mg] | Specific activity [IU/mg] |
| Starting solution: | 528 | 22.55 | 23.41 |
| Residual solution: | 394 | 17.14 | 22.99 |
| Rinsing solution: | 9 | 0.39 | 23.08 |
| Bonded | 125 (100%) | 5.02 | |
| Eluted: | 122 (97.6%) | 2.77 | 44.04 |

*International units (1 micromol conversion/minute under standard conditions)

As can be seen from Table 1, almost all the adsorbed hexokinase activity was also eluted again, the specific activity of the hexokinase being almost doubled. The hexokinase is of course not yet purified to homogeneity in this purification stage.

II. Adsorption of albumin

Human albumin (Serva, Order No. 11870), dissolved in 50 ml of 100 mM KCl in 50 mM TRIS-HCl buffer pH 7.0, is absorbed by pumping in circulation over the membrane. After the module has been washed with the same buffer (2×50 ml), the desorption is carried out with 50 ml of 1.5 M HCl solution in 50 mM phosphate buffer pH 7.0. The results are summarized in Table 2.

TABLE 2

| Albumin from human serum | Protein [mg] |
|---|---|
| Starting solution (50 ml) | 22.10 |
| Residual solution (50 ml) | 4.45 |
| Rinsing solution 1 (50 ml) | 6.06 |
| Rinsing solution 2 (50 ml) | 1.11 |
| Bonded | 10.48 |
| Eluted | 10.43 |

As can be seen from Table 2, all the adsorbed albumin is also desorbed again.

c) Regeneration of the module

Cleaning can indeed be carried out analogously to Blue Sepharose (for example from Pharmacia) using 0.1 M TRIS buffer pH 9.3 and acetate buffer pH 3.2 with a reduced efficiency and over a longer period of time. However, cleaning with 0.1 N-NaOH or 1 N HCl, which the derivatized membrane surprisingly withstands without damage (pH=1 and 13), is considerably more effective. During cleaning with acid, a reversible change in color takes place from blue to red, which is to be attributed to protonation of the aromatic system of Cibacron Blue. Because of the very stable bonding of the matrix and dyestuff, no measurable amount of dyestuff is split off under these conditions. The module cleaned in this way corresponds to the new state.

General comments: The protein contents are tested by the biuret method. The hexokinase activity is determined in accordance with H.U. Bergmeyer, Methoden der enzymatischen Analyse [Methods of enzymatic analysis], 3rd edition (1974), Verlag Chemie, Weinheim, pages 502–503.

EXAMPLE 25

Recharging with covalently immobilized enzyme

The flat membrane is rendered hydrophilic by a procedure analogous to that described in Example 21. The membrane (effective area 32 cm², effective weight 0.31 g, 0.014 m equivalent of $NH_2$ groups/g of membrane) is then reacted with 10% strength glutaric dialdehyde solution in 10 mM phosphate buffer pH 7.0 at room temperature for hour. The invertase solution (E.C.3.2.1.26; from yeast, Boehringer Mannheim, Cat. No. 104922, specific activity 330 U/mg) in !0 mM acetate buffer pH 4.6 is filtered in excess in circulation through the activated membrane overnight. Under these conditions, the catalytic activity of the immobilized invertase is retained almost completely.

To charge the membrane with protein again, for example after a protein denaturation, the membrane is again subjected to the aminolysis from Example 2!. The second charging of the membrane with invertase is carried out under the same conditions as above.

1st immobilization:

| | |
|---|---|
| Starting solution: | 3060 IU |
| Residual solution, not immobilized: | 1680 IU |
| Immobilized invertase: | 1380 IU |
| 2nd immobilization: | |
| Starting solution: | 2510 IU |
| Residual solution: | 1180 IU |
| Immobilized invertase: | 1330 IU |

What is claimed is:

1. A membrane comprising a homogeneous mixture of 70 to 98 percent by weight of polyvinylidene fluoride and 2 to 30 percent by weight of a polymer which can be rendered hydrophilic by chemical reaction formed essentially from polymethyl and/or polyethyl acrylate, said membrane having a maximum pore size in the range from 0.005 to 10 μm.

2. A membrane as claimed in claim wherein said maximum pore size is in the range from 0.01 to 2 μm.

3. A membrane as claimed in claim 2, wherein said maximum pore size is in the range of 0.05 to 0.8 μm.

4. A membrane as claimed in the polyvinylidene fluoride has an average weight (weight-average) of 30,000 to 500,000, and said polymer has an average molecular weight of 5,000 to 1,000,000.

5. A membrane as claimed in claim 4, wherein the polyvinylidene fluoride has an average molecular weight of 50,000 to 500,000 and said polymer has an average molecular weight of 50,000 to 200,000.

6. A membrane as claimed in claim i, which comprises a homogeneous mixture of 80 to 95% by weight of polyvinylidene fluoride and 5 to 20% by weight of said polymer.

7. A membrane as claimed in claim which contains 0.001 to 10 milliequivalents/g of membrane of at least one of the hydrophilic functional groups selected from the group consisting of —OH, —NH$_2$ and —COOH groups on a total surface of said membrane.

8. A membrane as claimed in claim 7, which contains 0.01 to 5 milliequivalents/g of membrane of said at least one of said hydrophilic functional groups on said total surface.

9. A membrane as claimed in claim 7, further comprising an immobilized biochemically active compound.

10. A membrane as claimed in claim 7, wherein said membrane is a flat or capillary membrane.

* * * * *

UNITED STATES PATENT AND TRADEMARK OFFICE
CERTIFICATE OF CORRECTION

PATENT NO. : 5,066,401

DATED : November 19, 1991

INVENTOR(S) : Heniz-Joachim MULLER et al

It is certified that error appears in the above-identified patent and that said Letters Patent is hereby corrected as shown below:

Col. 2, line 23, change "weight However" to --weight. However--;

line 68, after "invention" insert --.--.

Col. 3, line 11, change "3!6-70." to --316-70.--;

line 14, change "1000:and" to --1000:1 and--.

Col. 4, line 34, change "I0" to --10--.

Col. 5, line 2, change "having to 3" to --having 1 to 3--;

line 13, change "of to 30" to --of 1 to 30--.

Col. 6, line 31, change "10 or by" to --10 or 20% by--.

Col. 7, line 19, change "OH" to --OH--;

line 26, change "for to 30" to --for 1 to 30--.

Col. 8, line 5, change "I,3-" to --1,3---.

Col. 10, line 15, change "I60°C." to --160°C.--;

line 18, change "10µg" to --100 g--;

line 33, change "I60°C." to --160°C.--;

line 36, change "I00 g" to --100 g--;

line 52, change "I60°C." to --160°C.--.

UNITED STATES PATENT AND TRADEMARK OFFICE
CERTIFICATE OF CORRECTION

PATENT NO. : 5,066,401

DATED : November 19, 1991

INVENTOR(S) : Heniz-Joachim MULLER et al

It is certified that error appears in the above-identified patent and that said Letters Patent is hereby corrected as shown below:

Col. 11, line 26, change "I50 g" to --150 g--;

line 30, change "I60°C." to --160°C.--;

line 34, change "!00 g" to --100 g--.

line 48, delete "as";

lines 50-51, delete "passing through the membrane".

Col. 13, line 24, change "ar" to --are--;

line 30, change "I2 g" to --12 g--.

Col. 15, line 28, change "I20°C." to --120°C.--.

Col. 16, line 19, change "!40°C." to --140°C.--; change "I%" to --1%--;

line 37, change "EXAMPLE 6" to --EXAMPLE 16:--.

Col. 17, line 4, change "I50 ml" to --150 ml--;

line 20, change "EXAMPLE 8" to --EXAMPLE 18:--;

line 29, change "5" to --15--;

line 30, change "I0" to --10--;

line 33, change "!00" to --100--.

Col. 18, line 22, change "I40°C." to --140°C.--;

line 39, change "!6" to --16--.

Col. 19, line 48, change "H 5!25)" to --H 5125--.

UNITED STATES PATENT AND TRADEMARK OFFICE
CERTIFICATE OF CORRECTION

PATENT NO. : 5,066,401

DATED : November 19, 1991

INVENTOR(S) : Heniz-Joachim MULLER et al

It is certified that error appears in the above-identified patent and that said Letters Patent is hereby corrected as shown below:

```
Col. 20,   line 5, change "TRIS-HCI" to --TRIS-HCl--;

line 28, change "N-NaOH" to --N NaOH--;

line 54, after "for" insert --1--;

line 56, change "l0" to --10--;

line 63, change "2!" to --21--.

Claim 2, col. 21, line 19, after "claim" insert --1--.

Claim 4, col. 21, line 23, after "in" insert --claim 3,
wherein--.

Claim 6, col. 22, line 7, change "i" to --1--.

Claim 7, col. 22, line 11, after "claim" insert --1--.

Claim 9, col. 22, line 20, change "7" to --1--.
```

Signed and Sealed this

Twenty-fifth Day of May, 1993

Attest:

MICHAEL K. KIRK

*Attesting Officer*     *Acting Commissioner of Patents and Trademarks*